US012721570B2

(12) United States Patent
Maekawa et al.

(10) Patent No.: US 12,721,570 B2
(45) Date of Patent: Sep. 1, 2026

(54) TOUCHING EVALUATION DEVICE, AND TOUCHING EVALUATION METHOD

(71) Applicant: AEGLE LLC., Hyogo (JP)

(72) Inventors: Tomoko Maekawa, Hyogo (JP); Takayo Mitani, Hyogo (JP); Hiroyuki Tatsumi, Hyogo (JP)

(73) Assignee: AEGLE LLC., Hyogo (JP)

( * ) Notice: Subject to any disclaimer, the term of this patent is extended or adjusted under 35 U.S.C. 154(b) by 564 days.

(21) Appl. No.: 18/255,629

(22) PCT Filed: Dec. 9, 2021

(86) PCT No.: PCT/JP2021/045423

§ 371 (c)(1),
(2) Date: Jun. 2, 2023

(87) PCT Pub. No.: WO2022/124384

PCT Pub. Date: Jun. 16, 2022

(65) Prior Publication Data

US 2024/0016448 A1 Jan. 18, 2024

(30) Foreign Application Priority Data

Dec. 10, 2020 (JP) ................................ 2020-205224

(51) Int. Cl.
*A61B 5/00* (2006.01)

(52) U.S. Cl.
CPC .... *A61B 5/4827* (2013.01); *A61B 2562/0247* (2013.01)

(58) Field of Classification Search
CPC .......... G09B 19/00; G09B 9/00; G09B 23/28; A61B 5/01; A61B 5/4827; A61B 2562/0247

(Continued)

(56) References Cited

FOREIGN PATENT DOCUMENTS

JP 2005-352927 A 12/2005
JP 2010-286558 A 12/2010

(Continued)

OTHER PUBLICATIONS

Jo Byung Woo, KR 101775691 B1, "System for Providing Health Information Using In-shoe Pressure Measurement", Date Published: Sep. 6, 2017 (Year: 2017).*

(Continued)

*Primary Examiner* — John H Le
(74) *Attorney, Agent, or Firm* — Renner, Otto, Boisselle & Sklar, LLP

(57) ABSTRACT

Measurement control part measures contact pressures and a contact speed of a hand of a contacting person. The contact pressures change over time at respective positions, as measured values respectively based on two sensors when the hand of the contacting person touches sequentially to the two sensors being capable of detecting contact pressure. A determination control part compares measured values with reference ranges respectively, the reference range being a predetermined for a contacted person feeling comfortable when touched by the contacting person, and determines whether or not the measured value is within the reference range for each of measured values. An evaluation control part evaluates that the touching of the contacting person is a comfortable touching when all the measured values are within corresponding reference ranges respectively, and evaluates that the touching of the contacting person is an uncomfortable touching when one measured value is outside the corresponding reference range.

20 Claims, 13 Drawing Sheets

(58) Field of Classification Search
USPC .......................................................... 702/139
See application file for complete search history.

(56) References Cited

FOREIGN PATENT DOCUMENTS

| | | | |
|---|---|---|---|
| JP | 2012-34790 | A | 2/2012 |
| JP | 2012-37626 | A | 2/2012 |
| JP | 2013-134126 | A | 7/2013 |
| JP | 2016-87206 | A | 5/2016 |

OTHER PUBLICATIONS

International Search Report (ISR) (form 210) corresponding to counterpart International Patent Application PCT/JP2021/045423 mailed Feb. 1, 2022, with English translation.
Written Opinion of the International Searching Authority (WO/ISA) (form 237) corresponding to counterpart International Patent Application PCT/JP2021/045423 mailed Feb. 1, 2022, with partial English translation.

* cited by examiner

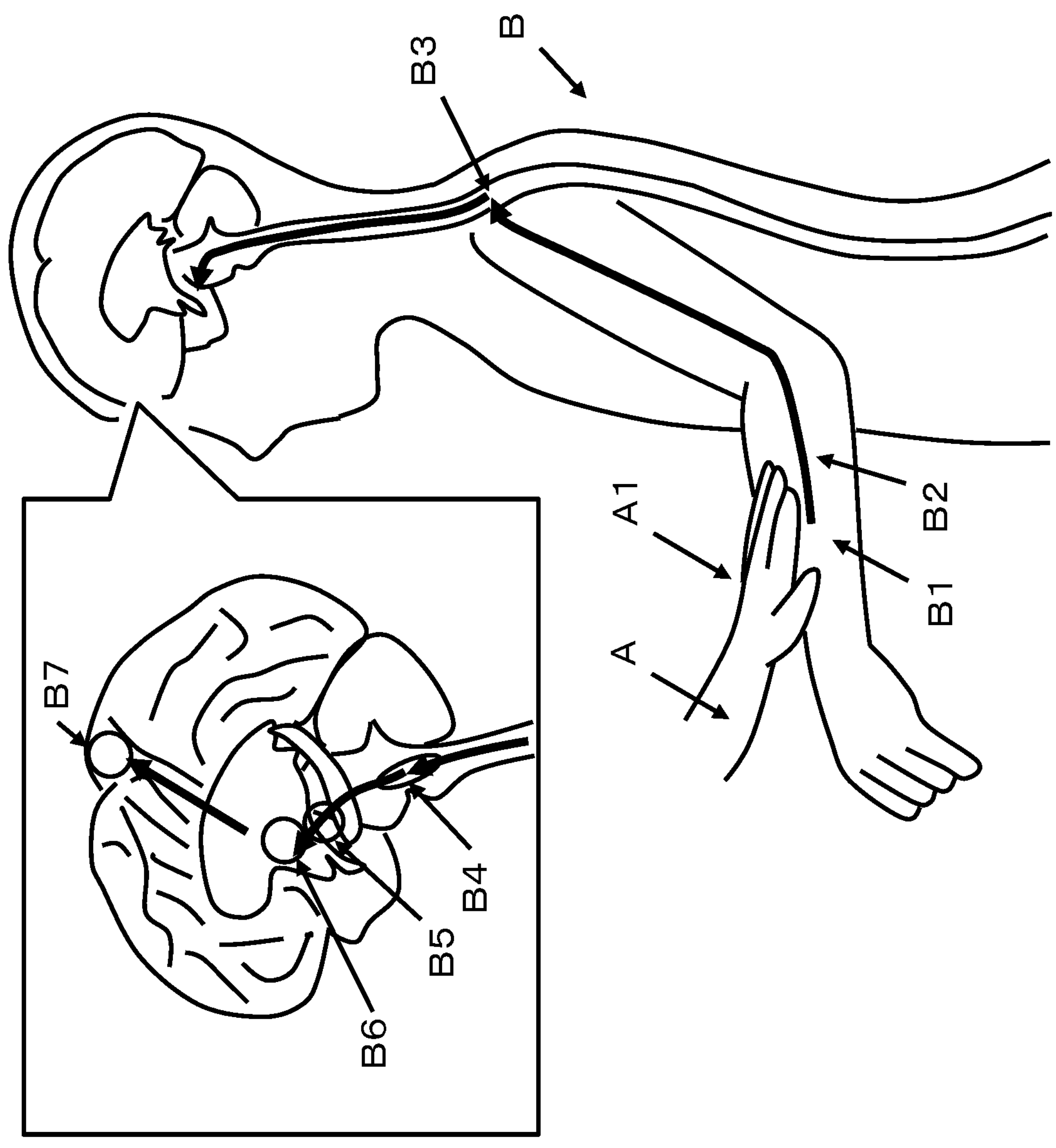
[Fig. 1]

[Fig. 2]
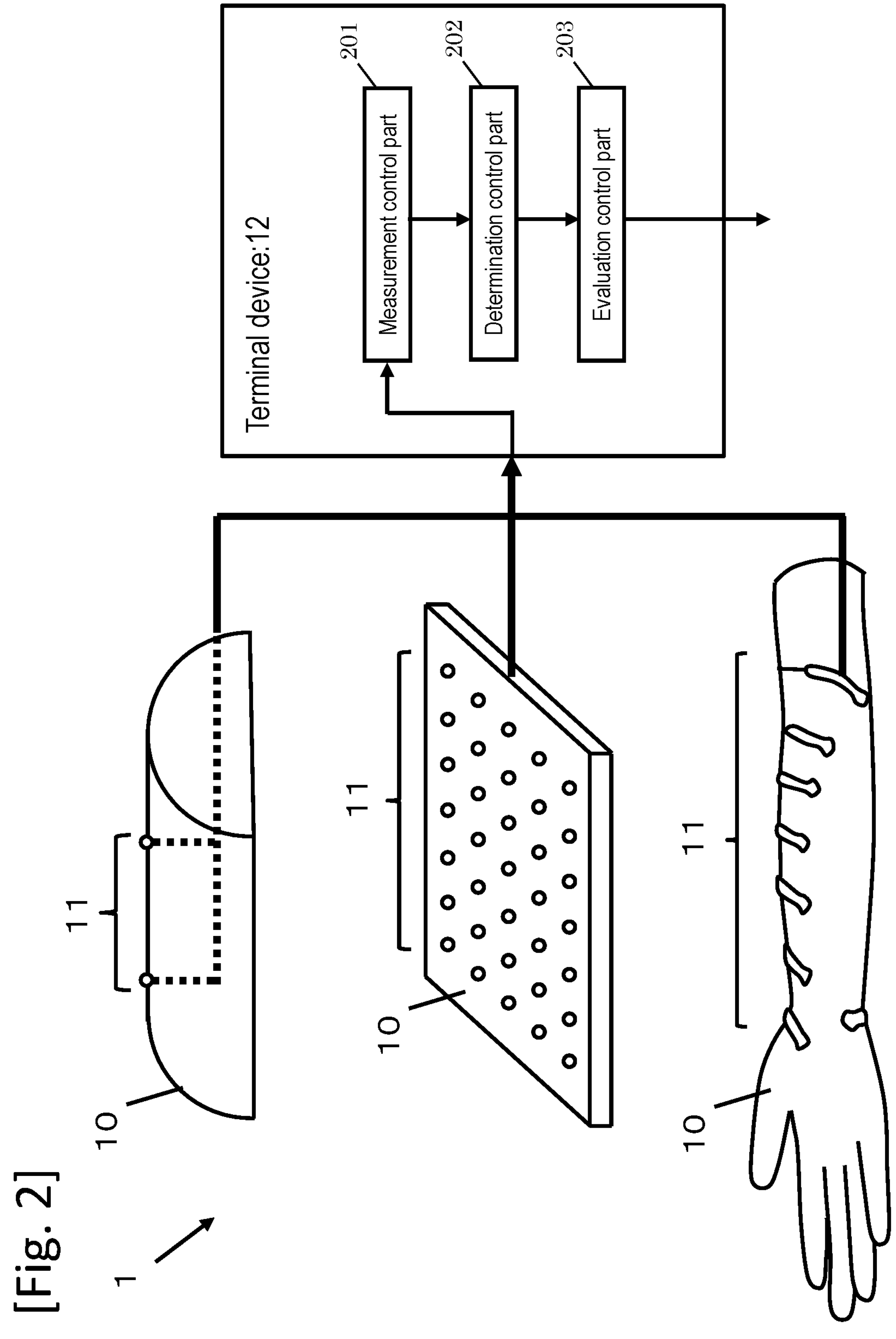

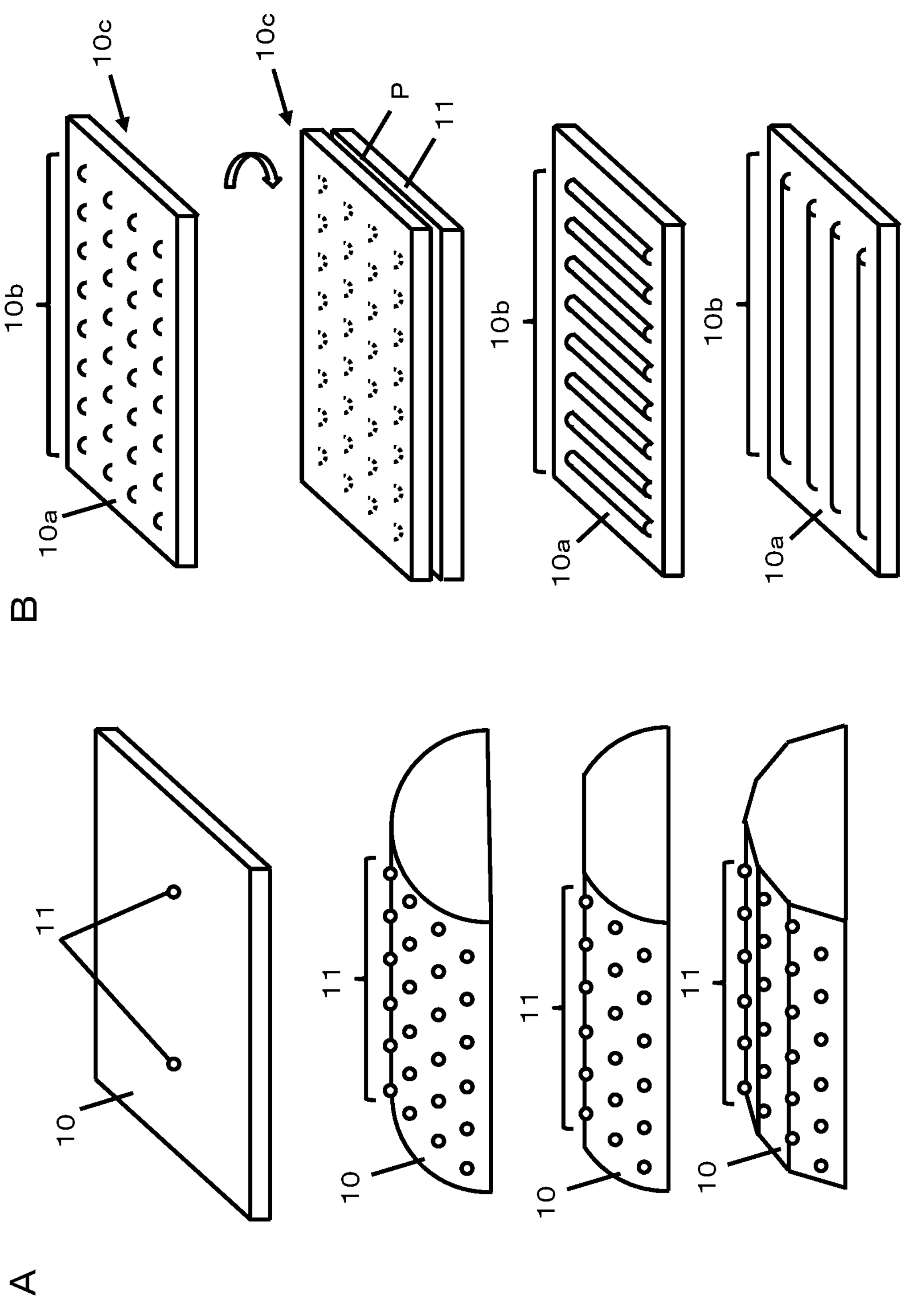
[Fig. 3]
A
B
10
11
10a
10b
10c
P

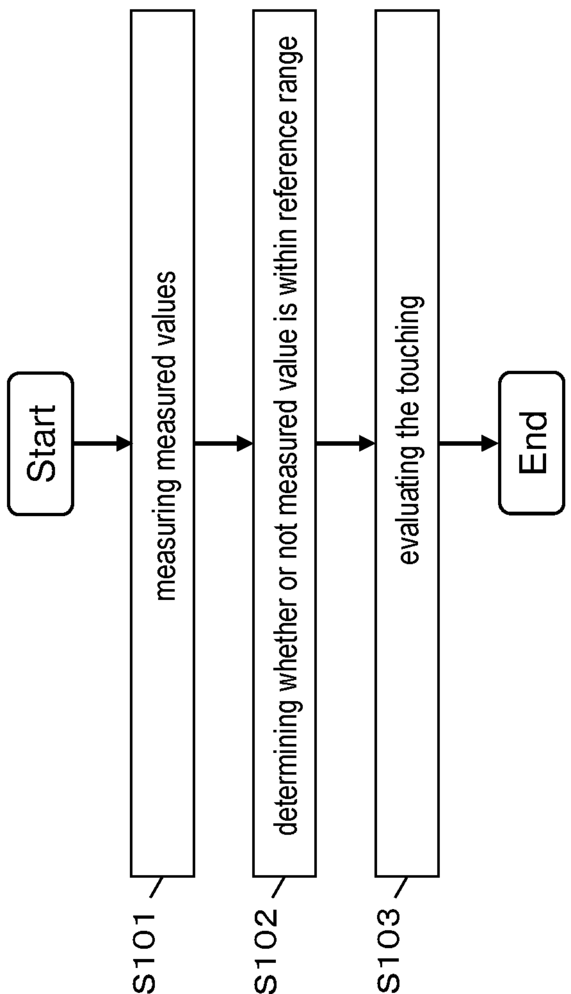
[Fig. 4]

[Fig. 5]
A
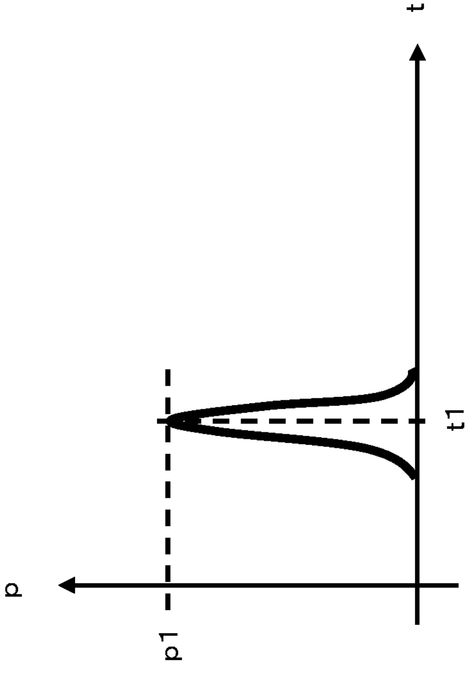
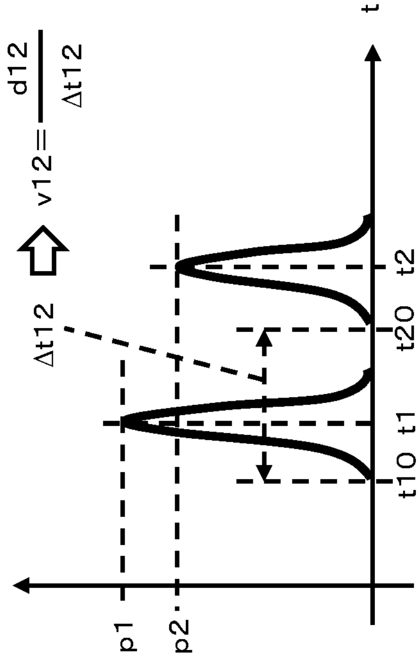
B
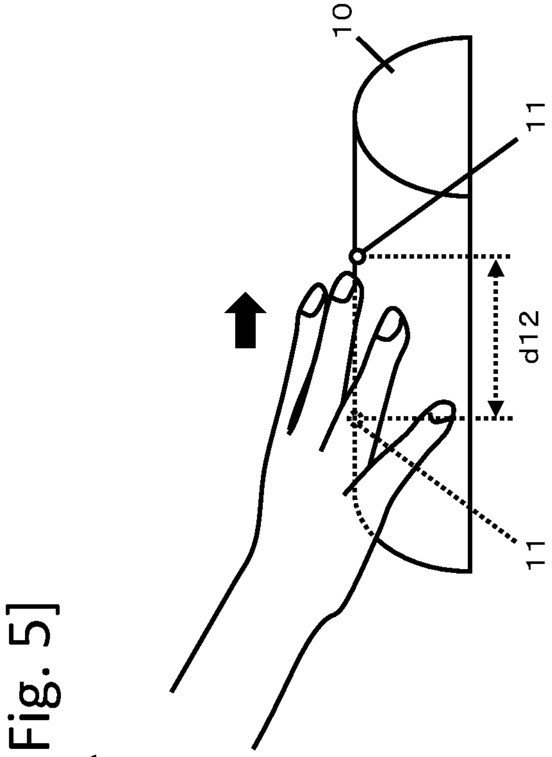
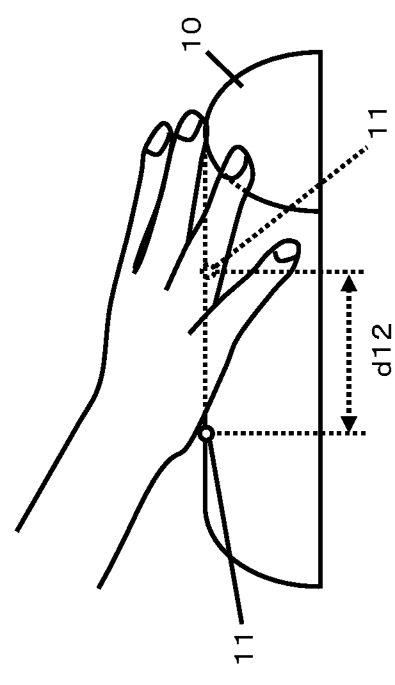

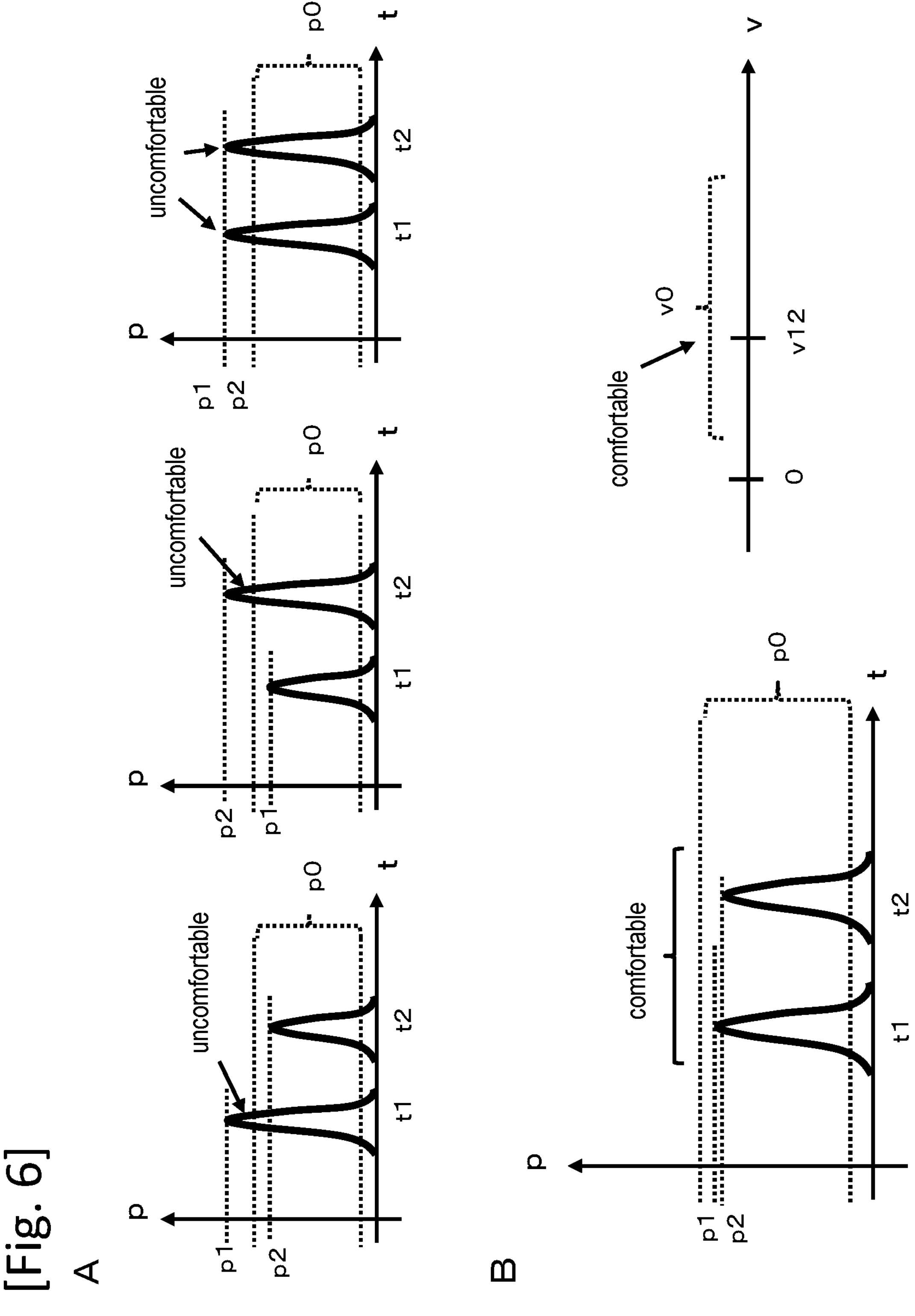
[Fig. 6]
A
uncomfortable
uncomfortable
uncomfortable
p
t
p0
p1
p2
t1
t2
B
comfortable
comfortable
v0
v12
0
v

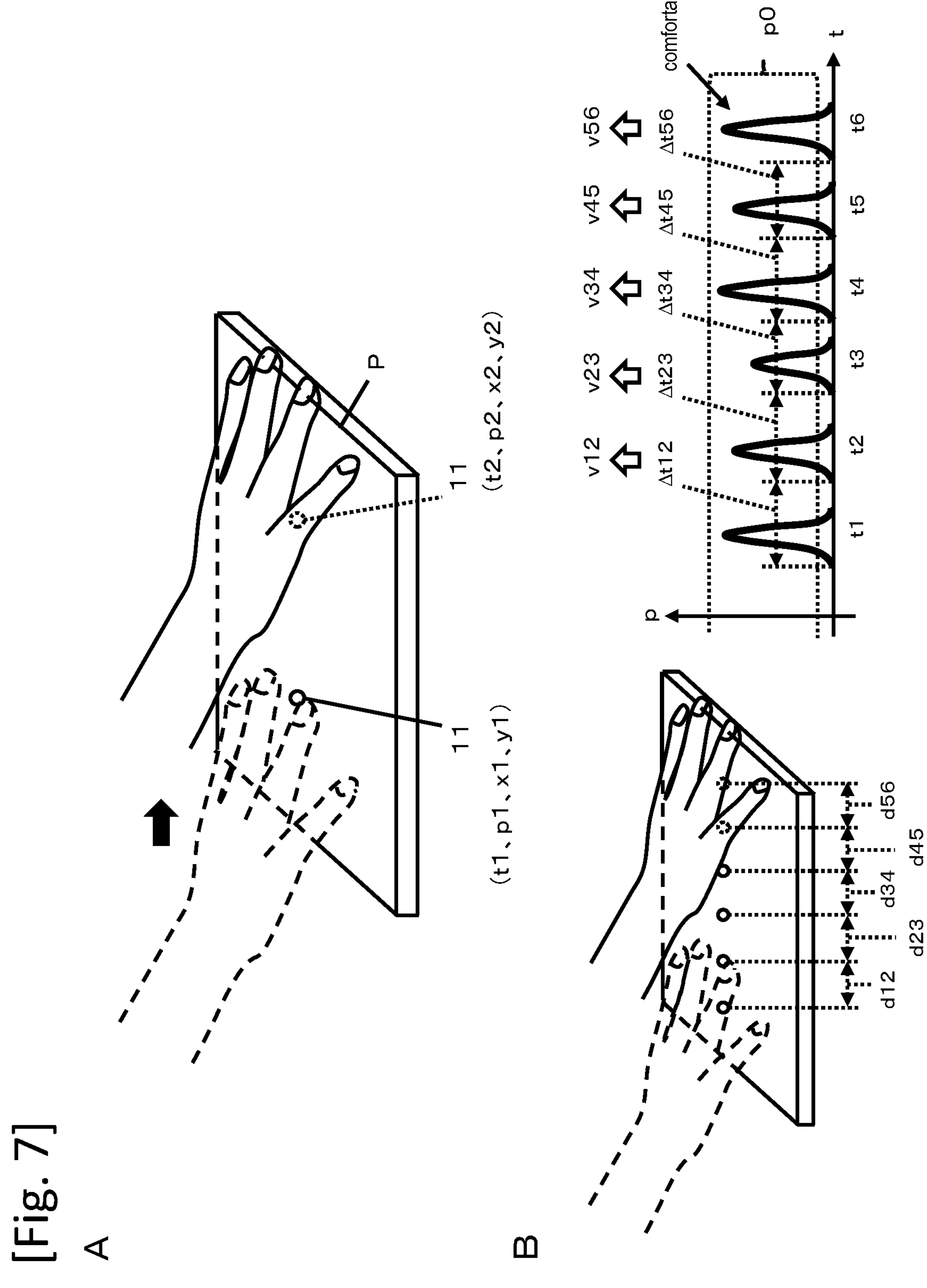
[Fig. 7]
A
B
P
11
(t1, p1, x1, y1)
(t2, p2, x2, y2)
d12
d23
d34
d45
d56
v12
v23
v34
v45
v56
Δt12
Δt23
Δt34
Δt45
Δt56
comfortable
p0
p
t
t1
t2
t3
t4
t5
t6

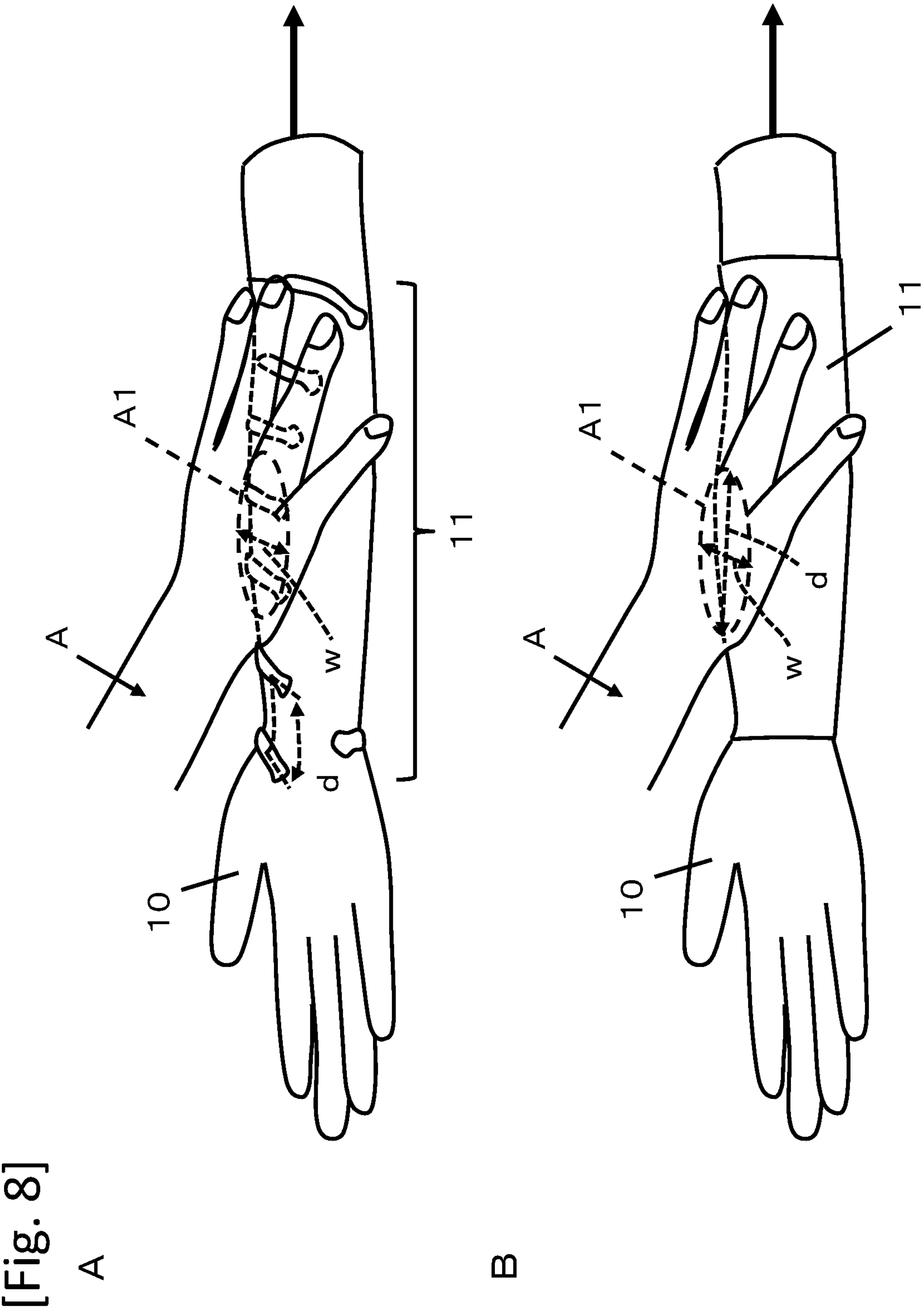
[Fig. 8]
A
B
A1
A
11
10
w
d
A1
A
11
10
w
d

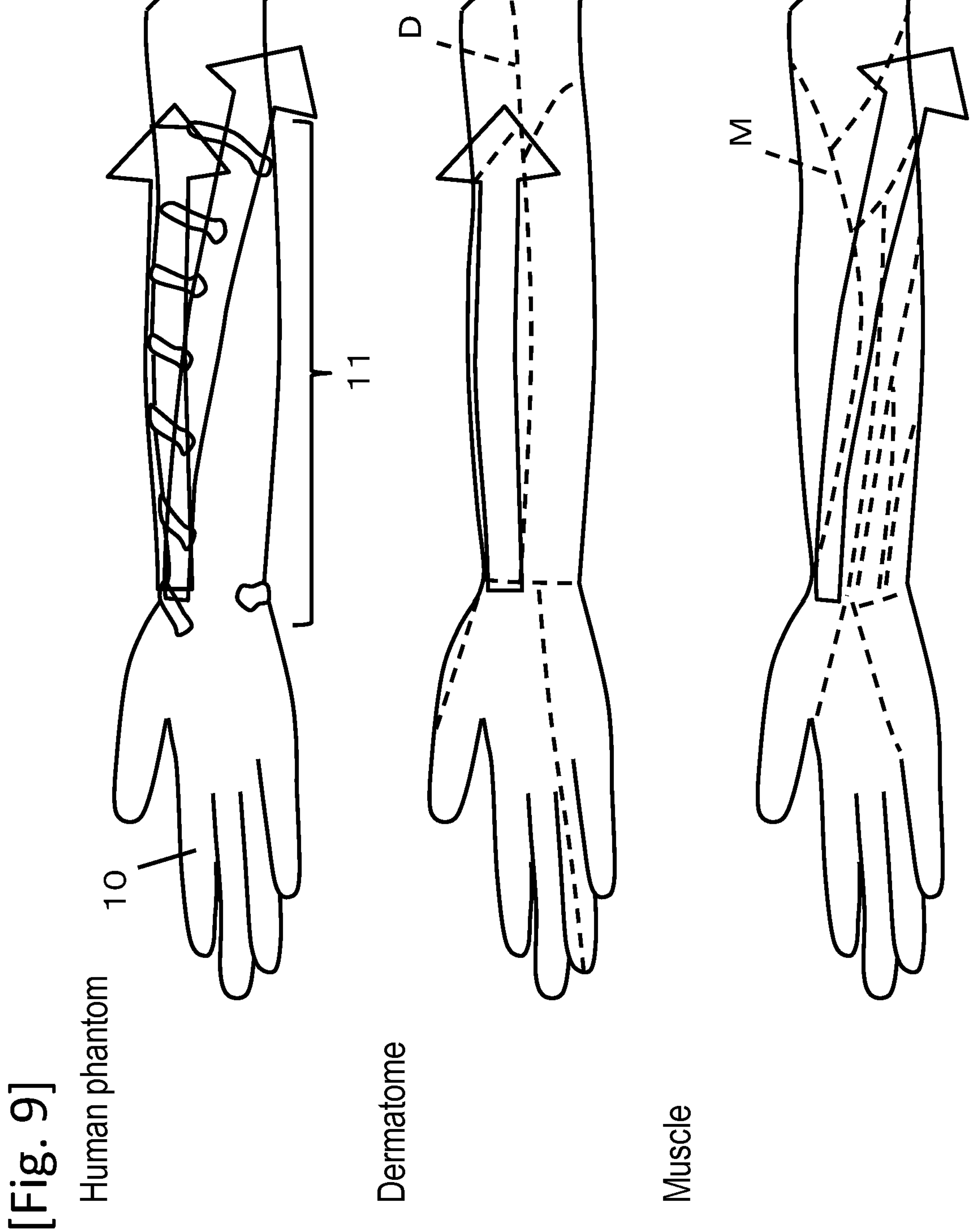
[Fig. 9]

[Fig. 10]

| | | Example 1 | Example 2 | Comparison example 1 | Example 3 | Example 4 | Comparison example 2 | Comparison example 3 | Comparison example 4 | Comparison example 5 | Comparison example 6 |
|---|---|---|---|---|---|---|---|---|---|---|---|
| Contact pressure ($kgf/cm^2$) | | 0.51 | 1.53 | 2.53 | 0.51 | 1.53 | 2.53 | 0.51 | 1.53 | 2.53 | 0.51 |
| Contact speed (cm/sec) | | 2 | 2 | 2 | 15 | 15 | 15 | 30 | 30 | 30 | 0.5 |
| Contact mode | | palm | palm | palm | palm | palm | palm | palm | palm | palm | palm |
| VAS | Before | 47.0 | 48.0 | 47.0 | 48.0 | 47.0 | 47.0 | 49.0 | 50.0 | 48.0 | 47.0 |
| | After | 61.5 | 60.0 | 30.0 | 62.0 | 61.0 | 33.0 | 34.0 | 33.0 | 31.0 | 32.0 |
| | difference | 14.5 | 12.0 | -17.0 | 14.0 | 14.0 | -14.0 | -15.0 | -17.0 | -17.0 | -15.0 |
| Comfort | | ○ | ○ | × | ○ | ○ | × | × | × | × | × |

[Fig. 11]

| | | Example 5 | Example 6 | Example 7 | Example 8 | Example 9 | Example 10 | Example 11 |
|---|---|---|---|---|---|---|---|---|
| Contact pressure ($kgf/cm^2$) | | 0.51 | 0.51 | 0.51 | 0.51 | 0.51 | 0.51 | 0.51 |
| Contact speed (cm/sec) | | 2 | 2 | 2 | 2 | 2 | 2 | 2 |
| Contact temperature (degrees) | | 30 | 35 | 20 | 30 | 30 | 30 | 30 |
| Contact attachment (cm2) | | 52.5 | 52.5 | 52.5 | 8.0 | 2.4 | 119.0 | 52.5 |
| Contact mode | | palm | palm | palm | three fingers | one finger | palm and five fingers | palm |
| Contact route | | on line | on line | on line | on line | on line | on line | off-line |
| VAS | Before | 48.0 | 47.0 | 47.0 | 50.0 | 49.0 | 47.0 | 47.0 |
| | After | 70.0 | 71.0 | 58.0 | 70.0 | 69.0 | 70.0 | 58.0 |
| | difference | 22.0 | 24.0 | 11.0 | 20.0 | 20.0 | 23.0 | 11.0 |
| Comfort | | A | A | ○ | A | A | A | ○ |

[Fig. 12]

| | | Example 12 | Example 13 | Comparison example 7 | Example 14 | Example 15 | Comparison example 8 | Comparison example 9 |
|---|---|---|---|---|---|---|---|---|
| Contact pressure (kgf/cm$^2$) | | 0.10 | 0.30 | 1.20 | 0.50 | 0.50 | 0.50 | 0.50 |
| Contact speed (cm/sec) | | 2 | 2 | 2 | 1 | 2 | 10 | 30 |
| Contact mode | | three fingers | three fingers | three fingers | three fingers | three fingers | three fingers | three fingers |
| VAS | Before | 46.0 | 52.5 | 50.0 | 47.0 | 48.0 | 50.5 | 47.5 |
| | After | 68.0 | 70.0 | 34.5 | 52.5 | 64.0 | 62.5 | 39.0 |
| | difference | 22.0 | 17.5 | -15.5 | 5.5 | 16.0 | 12.0 | -8.5 |
| Comfort | | ○ | ○ | × | ○ | ○ | ○ | × |

[Fig. 13]

| | | Example 16 | Example 17 | Example 18 | Comparison example 10 | Comparison example 11 | Comparison example 12 | Example 19 |
|---|---|---|---|---|---|---|---|---|
| Contact pressure ($kgf/cm^2$) | | 0.51 | 0.51 | 0.51 | 0.51 | 0.51 | 0.51 | 0.51 |
| Contact speed (cm/sec) | | 2 | 2 | 2 | 2 | 2 | 2 | 2 |
| Contact temperature (degrees) | | 32.5 | 32.5 | 32.5 | 32.5 | 32.5 | 22 | 41 |
| Contact attachment (cm2) | | 2.4 | 8.0 | 52.5 | 119.0 | 0.5 | 8.0 | 8.0 |
| Contact mode | | one finger | three fingers | palm | palm and five fingers | tip of nail | three fingers | three fingers |
| VAS | Before | 51.0 | 38.0 | 48.0 | 53.0 | 50.0 | 47.0 | 49.5 |
| | After | 62.0 | 58.5 | 67.5 | 51.0 | 32.5 | 33.0 | 62.0 |
| | difference | 11.0 | 20.5 | 19.5 | -2.0 | -17.5 | -14.0 | 12.5 |
| Comfort | | ○ | A | ○ | × | × | × | ○ |

TOUCHING EVALUATION DEVICE, AND TOUCHING EVALUATION METHOD

This application is a national phase of International Application No. PCT/JP2021/045423 filed Dec. 9, 2021, which claims priority to Japanese Patent Application No. 2020-205224 filed Dec. 10, 2020, in the Japan Patent Office, which are hereby incorporated herein by reference.

TECHNICAL FIELD

The present invention relates to a touching evaluation device and a touching evaluation method.

BACKGROUND ART

Touching is one of a nonverbal communication and says that a contacting person touches to a body of a patient with a palm. The touching is a touching for a purpose of medical treatment such as massage and acupressure, a touching for a purpose of treatment such as measurement of vital signs, cleaning and examination, and a sympathetic touching centered on communication such as relief of pain/anxiety and encouragement.

When supporters such as nurses touch to a body such as hand or arm of a patient who suffered from a disease such as terminal cancer or dementia with a palm and they relieve the pain and anxiety of the patient's fight against illness, it is the sympathetic touching. By the supporters touching to the patient gently, it is possible to reduce pain, anxiety, depression, loneliness, tension, etc. of the patient, to stimulates the parasympathetic nervous system, and to lead the patient to mental and physical stability.

In recent years, a development of instruments such as measuring pressing force has progressed. For example, a JP-A-2005-352927 (Patent Literature 1) discloses an input device having a sheet sensor, a controller, an actuator and drive means. A JP-A-2012-34790 (Patent Literature 2) discloses a contact pressure measurement system measuring a contact pressure in a body tissue. A JP-A-2013-134126 (Patent Literature 3) discloses a bio signal detector having a support, a pressure sensor and a flexible material.

CITATION LIST

Patent Literature

[Patent Literature 1] JP-A-2005-352927
[Patent Literature 2] JP-A-2012-34790
[Patent Literature 3] JP-A-2013-134126

SUMMARY OF INVENTION

Technical Problem

The sympathetic touching is carried out not only in educational settings, but also in hospitals, nursing homes, baby touching, baby massage, children's emotional education, beauty, etc. In order to spread comfortable touching to the contacting person at various locations, it is necessary to clarify a reference (standard) for making a contacted person feel comfortable even if anyone does touches, to evaluate the touching of the contacting person, and to ensure a repeatability of the touching based on the reference.

However, at present, there is no clear references for the contacted person to feel comfortable being touched by the contacting person, and there was a problem that a comfortable touching can not be evaluated with high accuracy.

Accordingly, the present invention was created as a solution for the problem and aims at providing a touching evaluation device and a touching evaluation method that can evaluate a touching with high accuracy based on a reference of the touching to cause comfort.

Solution to Problem

A touching evaluation device of the present invention comprises a measurement control part, a determination control part, and an evaluation control part. The measurement control part measures contact pressures and a contact speed of a hand of a contacting person, the contact pressures changing over time at respective positions, as measured values respectively based on two sensors when the hand of the contacting person touches sequentially to the two sensors being capable of detecting a contact pressure in at least two different positions. The determination control part compares the measured values with reference ranges respectively, the reference range being a predetermined for a contacted person feeling comfortable when touched by the contacting person, and determining whether or not the measured value is within the reference range for each of measured values. The evaluation control part evaluating that the touching of the contacting person is a comfortable touching when all the measured values are within corresponding reference ranges respectively, and evaluating that the touching of the contacting person is an uncomfortable touching when one measured value is outside the corresponding reference range. A pressure reference range corresponding to the contact pressure for the touching of a whole body except a face of the contacting person is a range of 0.001 kgf/cm2-2.000 kgf/cm2, and the pressure reference range for the touching of the face is a range of 0.001 kgf/cm2-1.000 kgf/cm2. A contact reference speed corresponding to the contact speed is a range of 1 cm/sec-20 cm/sec.

A touching evaluation method of the present invention comprises a measurement control step, a determination control step, and an evaluation control step. Each control step of the touching evaluation method corresponds to each control part of the touching evaluation device.

Advantageous Effects of Invention

According to this invention, it is possible to evaluate a touching with high accuracy based on a reference of the touching to cause comfort.

BRIEF DESCRIPTION OF DRAWINGS

FIG. 1 is an outline diagram indicating an example from a touching of a contacting person to a contacted person feeling comfort according to the present invention.

FIG. 2 is a functional block diagram indicating an example of a touching evaluation device according to the present invention.

FIG. 3A is an outline diagram indicating an example of a touching base material according to the present invention.

FIG. 3B is an outline diagram indicating an example of a touching assistance base material according to the present invention.

FIG. 4 is a flowchart indicating execution steps of a touching evaluation method according to the present invention.

FIG. 5A is a perspective view indicating an example of a graph indicating a change over time of a first touching of the contacting person and a contact pressure according to the present invention.

FIG. 5B is a perspective view indicating an example of a graph indicating a change over time of a second touching of the contacting person and a contact pressure according to the present invention.

FIG. 6A is three types of graphs indicating a change over time of a contact pressure including an uncomfortable touching.

FIG. 6B is a graph indicating a change over time of the contact pressure indicating a comfortable touching and contact speed.

FIG. 7A is a perspective view of an example of a touching when a touching base material and a sensor are touch panel type devices.

FIG. 7B is a graph indicating a change over time of touching and contact pressure when six sensors are installed on the touching base material.

FIG. 8A is a perspective view of an example of an installation form of plural spot compound sensors according to the present invention.

FIG. 8B is a perspective view of an example of an installation form of a sheet compound sensor according to the present invention.

FIG. 9 is a perspective view of an example of a relation with a forearm human phantom, dermatome and muscle, and a specific line according to the present invention.

FIG. 10 is a table indicating an evaluation condition and an evaluation result of touching of Example 1-4 and Comparison example 1-6.

FIG. 11 is a table indicating an evaluation condition and an evaluation result of touching of Example 5-11.

FIG. 12 is a table indicating an evaluation condition and an evaluation result of touching of Example 12-15 and Comparison example 7-9.

FIG. 13 is a table indicating an evaluation condition and an evaluation result of touching of Example 16-19 and Comparison example 10-12.

DESCRIPTION OF EMBODIMENTS

The preferred embodiments of the present invention will be explained below according to the attached drawings; thereby the present invention will be clearly understood. The embodiments below are examples materializing the present invention, and do not limit the technical scope of the present invention.

For touching, it is important that a contacted person feels comfortable when a contacting person touches to the contacted person. When the contacting person touches to the contacted person, a skin sensation of the contacted person transmits to a brain of the contacted person via nerves of the contacted person, and affects a whole body of the contacted person.

Specifically, as shown in FIG. 1, for example, at first when a contacting person A carries out touching by a hand (specifically contact surface A1 of a palm) to skin B1 of a forearm of a contacted person B, non-discriminative tactile and heat/cold sensory receptors presenting on the skin B1 of the contacted person B react and emit signals, and nerves B2 connected to the sensory receptors and transmitting skin sensation transmit the signals to nerves B3 of the spinal cord. Next, the nerve B3 transmit the most of the signals to brainstem reticular formation B4.

The signals transmitted to the brainstem reticular formation B4 transmit to amygdala B5 (limbic system), thalamus, hypothalamus, insular cortex B6, etc., and promote mentally relax to the brain in the amygdala B5 and insular cortex B6. At the same time, the signals affect autonomic nervous system in the insular cortex B6, activate parasympathetic nervous system, and promote a decrease in blood pressure and a decrease in heart rate. Also, the signals transmitted to the thalamus transmit throughout the brain. Some signals of the signals transmit to the primary somatosensory area B7, and the contacted person B recognizes which position of his/her body has been touched.

Here, the tactile of the contacted person B by the touching of the contacting person A transmits to the brain through nerve B2, B3 transmitting skin sensation of the sensory receptors, and affects the whole body of the contacted person B. Particularly, for the tactile on of the contacted person B by the touching of the contacting person A, a soft and slow speed specific stimulation reacts the sensory receptors on the skin B1 of the contacted person B, and effectively promotes reduction of anxiety and fear in the amygdala B5, the insular cortex B6, and the hypothalamus B6, and the adjustment of the autonomic nerve. This is a comfort that contacted person B feels by the touching.

The present inventors of the present invention have been studying the comfort of contacted person B by the touching of the contacting person A for many years. In order to cause a series of reactions in the contacted person B by touching in a short time, and to maximize the reduction of anxiety and tension, and the enhancement of the parasympathetic nervous system, the present inventors found that a contact pressure and a contact speed of a hand of the contacting person A (for example, contact surface A1 of palm) are important based on Examples and Comparative examples described later. The present inventors invented a device and a method for evaluating touching based on Examples and Comparative examples.

Namely, as shown in FIG. 2, a touching evaluation device 1 according to the present invention comprises a touching base material 10, at least two sensors 11, and a terminal device 12. The two sensors 11 are sensors of the minimum number to detect contact pressure and contact speed. The touching base material 10 is the object touched by the contact person A. There is not the limitation in particular if the touching base material 10 can install two sensors 11. For example, as shown in FIG. 2, the touching base material 10 may be configured in a semi-cylindrical shape, and two sensors 11 may be installed at a predetermined interval on an outer peripheral surface of the semi-cylindrical shape. The touching base material 10 and the sensors 11 may be configured by forming the touching base material 10 into a rectangular parallelepiped sheet arranging two or more sensors 11 on the sheet 10 at a predetermined interval. As shown in FIG. 3, the touching base material 10 and the two sensors 11 may be configured by forming the touching base material 10 into a rectangular parallelepiped and arranging the two sensors 11 on the sheet 10. The shape of the touching base material 10 is not particularly limited. Two or more sensors 11 may be arranged at a predetermined interval on an outer peripheral surface of the touching base material 10 configured in a semi-cylindrical shape. In addition, the touching base material 10 may be configured by horizontally cutting at a part located on an upper surface of a semi-cylinder with a plane forming a diameter of the semi-cylinder as a bottom surface, and two or more sensors 11 may be arranged at an equal interval on an outer peripheral surface or a cut surface of the semi-cylinder. The touching base material 10 may be formed into half polygon such as half square prism, half pentagonal prism, half hexagonal prism, half octagonal prism, half decagonal prism, half decahexagonal prism and the like, in addition to semi-elliptical prism. In that case, two or more sensors 11 are arranged on these outer peripheral surfaces.

When two or more sensors 11 are composed of a touch panel type terminal device 12 capable of measuring pressure and position of touching, the touch panel type terminal device 12 may be used as the touching base material 10 and the sensors 11. For example, the terminal device 12 in this case may be a tablet terminal device, a touch panel type mobile terminal device or the like. The touch panel of the terminal device 12 may be used as it as the sensors 11, and the touch panel functions as a pressure sensor and a position sensor. As shown in FIG. 3, for example, the touching base material 10 and the sensors 11 may be configured by preparing a touching assistance base material 10*c* in which plural protrusions 10*b* are arranged at a predetermined interval on a rectangular parallelepiped sheet 10*a*, and by arranging the touching assistance base material 10*c* on a touch panel P of the terminal device 12 with the plural protrusions 10*b* in contact with the contact surface of the touch panel P. In this case, when the contacting person touches to a surface of the touching assistance base material 10*c* on which the protrusions 10*b* are not present, a protrusion 10*b* contacts the touch panel P, and it is possible to measure contact pressure and contact speed of the hand of the contacting person. In this way, it is possible to utilize the touch panel type terminal device 12 owned by the contacting person as sensors, and to evaluate touching easily. In addition, the touching base material 10 and the touching assistance base material 10*c* are not particularly limited, and may be a flexible material such as synthetic resin or an elastic material such as sponge or rubber.

As shown in FIG. 2, the touching base material 10 may be composed as a human phantom of a right forearm. In this way, the contacting person A can touch to the contacted person B while being conscious of the contacted person B. The type of the human phantom is not particularly limited, and may include a left forearm, backs of left and right hand, left and right palms, face, whole body or the like.

The sensor 11 may be composed of a pressure sensor and an elastic compound sensor such as a sponge or the rubber. When the sensor is an elastic compound sensor, when the contacting person A touches to the elastic compound sensor 11 with the hand, the elastic compound sensor is recessed by the pressure of the hand, and it is possible to measure the contact pressure of the hand from the amount of recess.

When position intervals of the relative sensors 11 are known in an installation position of sensor 11, the installation position of sensor 11 is not particularly limited. As will be described later, when a contact path (contact route) of a running of the hand of the contacting person A on a skin of the contacted person B, it is preferred that a touching base material 10 is made into a human phantom 10 and the sensors 11 are installed at positions on a specific line having a predetermined width along dermatome or muscle run. In this way, it is possible to determine whether or not the hand of the contacting person A moves along the dermatome or the muscle run.

The installation method of the sensors 11 are not particularly limited. For example, as shown in FIG. 2, the sensors may be installed on the surface of the touching base material 10, or may be built inside the surface of the touching base material 10. A cover member may be separately provided to cover the two or more sensors 11 provided on the touching base material 10. The cover member may be an artificial leather that simulates human skin. In this way, the contacting person A can perform touching without a sense of discomfort.

The terminal device 12 is a computer used generally, and includes a mobile device with touch panel, a tablet type terminal device, a wearable model terminal device and the like. The terminal device 12 includes a memory part, an input part, and an output part. The input part is a keyboard, a mouse, touch panel or the like, and the output part is a liquid crystal display or the like.

The terminal device 12 have a built-in CPU (GPU), ROM, RAM, etc. (not shown), and the CPU uses the RAM as a work area, and executes program stored in the ROM or the like. Further, each control part described later also realizes a function of each control part by the CPU executing the program.

As shown in FIG. 2 and FIG. 4, a configuration and execution steps in an embodiment of the present invention are explained. First, a contacting person A or a leader instructing touching of the contacting person A inputs an evaluation key into a terminal device 12 to evaluate a touching of the contacting person A. Then a measurement control part 201 of the terminal device 12 starts two sensor 11, and displays a start of a touching to a touching base material 10 on a panel for the contacting person A.

When the contacting person A confirms the display of the panel, and touches to the touching base material 10 by a hand (e.g., a palm), the measurement control part 201 measures contact pressures of the hand of the contacting person A and a contact speed as measured values respectively based on two sensors 11 installed on the touching base material 10 (FIG. 4: S101).

The measurement method of the measurement control part 201 is not particularly limited. For example, when the contacting person A sequentially touches to the two sensors 11 on the touching base material 10, the two sensors 11 sequentially send signals responded to the touching of the hand of the contacting person A respectively, and the measurement control part 201 measures contact pressures of the hand and contact speed based on the signals from two sensors 11.

As shown in FIG. 5A, when the hand of the contacting person A touches to the first sensor 11 in the two sensors 11 of the touching base material 10, the measurement control part 201 measures a contact pressure p1 (kgf/cm2) of the hand of the contacting person A at the first time t1 (sec) based on a signal from the first sensor 11. When the hand of the contacting person A starts to touch to the first sensor 11, as shown in FIG. 5A, the contact pressure p (kgf/cm2) detected by the first sensor 11 gradually increases, and becomes the maximum value. Then, when the hand of the contacting person A starts to move away from the first sensor 11, the contact pressure p (kgf/cm2) gradually decreases, and becomes zero. The measurement control part 201 measures the maximum of the contact pressure p (kgf/cm2) detected in the shape of a mountain as a contact pressure p1 (kgf/cm2) of the hand of the contacting person A, and acquires that time as the first time t1 (sec).

Next, as shown in FIG. 5B, when the hand of the contacting person A continuously touches to the next second sensor 11 of the touching base material 10, the measurement control part 201 measures a contact pressure p2 (kgf/cm2) of the hand of the contacting person A at the second time t2 (sec) based on a signal from the second sensor 11. Here, the contact pressure p (kgf/cm2) detected by the second sensor 11, like the first sensor 11, starts in the shape of a mountain for the touching of the hand of the contacting person A. So, the measurement control part 201 measures the maximum of the contact pressure p (kgf/cm2) detected in the shape of a mountain as a contact pressure p2 (kgf/cm2) of the hand of the contacting person A, and acquires that time as the second time t2 (sec). In this way, when the hand of the contacting person A touches to the sensors 11 at two different positions, it is possible to measure the contact pressures p1 (kgf/cm2) and p2 (kgf/cm2) at each of positions of the hand of the contact person A as the contact pressure p (kgf/cm2) changing over time.

In general touching, when the first or final contact pressure may be too high, this may cause uncomfortable touching. Therefore, by measuring contact pressure p (kgf/cm2) changing over time at each position and by using for evaluation, it is possible to evaluate a habit of the touching of the contacting person A concretely.

In addition, the measurement control part 201 can measure the contact speed of the hand of the contacting person A passing the two sensors 11, by using a position interval d12 (cm) between the two sensors 11 and a time interval Δt12 (sec) at which the contact pressure (kgf/cm2) is detected by each of the two sensors 11. Specifically, the measurement control part 201 calculates a time interval Δt12 (sec) between a time t10 when a leading of the contact pressure p (kgf/cm2) detected by the first sensor 11 is started, and a time t20 when a leading of the contact pressure p (kgf/cm2) detected by the second sensor 11 is started, and divides a position interval d12 (cm) between two sensors 11 stored in advance in a predetermined memory by the time interval Δt12 (sec). In this way, it is possible to calculate the contact speed v12 (cm/sec) of the hand of the contacting A passed through the two sensors 11. The position interval d12 (cm) between the two sensors 11 is measured in advance.

When the measurement control part 201 completes the measurement, a determination control part 202 of the terminal device 12 compares the measured values with reference ranges respectively, the reference range being a predetermined for a contacted person B feeling comfortable when touched by the contacting person A, and determines whether or not the measured value is within the reference range for each of measured values (FIG. 4: S102).

The determination method of the determination control part 202 is not particularly limited. For example, the determination control part 202 refers to a predetermined memory when acquiring measured values. The memory stores reference ranges for each of measured values. The determination control part 202 acquires a pressure reference range corresponding to the contact pressure of the measured value, and determines whether or not the contact pressure is within the pressure reference range.

The pressure reference range is a range on the basis of a contact pressure of the touching that the contacted person B feels comfortable. Normally, the larger the contact pressure of touching, the higher the invasiveness to the contacted person B and the greater the burden on the contacted person B. When the contacted person B does not feel pain even if the contact pressure is large to some extent, the touching becomes comfortable. If the contact is made with such a contact pressure that the contacted person B feels pain, the touching becomes uncomfortable.

There is a report that a heart rate of the contacted person B changed due to the difference in the contact pressure of touching. The contact pressure of touching for the contacted person B to feel comfortable does not become a large pressure. For example, the contact pressure for touching a terminal cancer patient with a strong sense of fatigue is equal to or lower than a contact pressure for wiping (for example, 0.510 kgf/cm2-1.000 kgf/cm2). Some studies reported that C tactile fibers and hair receptors reacted at contact pressure of a range of 0.001 kgf/cm2-0.220 kgf/cm2. The C tactile fibers and hair receptors are tactile sensors that transmit comfort. By these tactile sensors reacting, the comfort is transmitted to the brain via nerves B2 and B3. In addition, a pressure sensor capable of detecting a contact pressure of 0.001 kgf/cm2 already exists.

In the present invention, when the touching is done on the whole body except the face, a pressure reference range is set in the range of 0.001 kgf/cm2-2.000 kgf/cm2. When the touching is done on the face, a pressure reference range is set in the range of 0.001 kgf/cm2-1.000 kgf/cm2. This is because the face has a higher density of tactile sensors than the whole body except the face. The touching within this pressure reference range results in extremely light contact or in comfortable contact with pressing compared to normal contact. In addition, the pressure sensor outputs a contact force (kgf) (N) as a measured value. In this case, the contact force may be used as a measured value, and the contact force may be compared with a force reference range corresponding to the pressure reference range for determination. The contact pressure may be calculated by dividing the output contact force by a contact area between the pressure sensor and the hand of the contacting person (or a detection area of a pressure sensor), and may be determined by comparing the calculated contact pressure with the pressure reference range.

As shown in FIG. 6A, the determination control part 202 displays a graph which assumed the contact pressure detected with the two sensors respectively as a vertical axis, and the graph assumed the time when the contact pressure is detected as a cross axle, and it is possible to draw two mountain-shaped graphs. The maximum value of the first mountain-shaped graph is the contact pressure p1 (kgf/cm2) measured by the first sensor 11, and the maximum value of the next mountain-shaped graph is the contact pressure becomes p2 (kgf/cm2) measured by the second sensor 11. For example, the determination control part 202 displays the touching mode of the body and the touching mode of the face selectably, and acquires the pressure reference range of the mode selected by contacting person A (here, the touching mode of the body). Then, the determination control part 202 sets the acquired pressure reference range p0 to the graph, and determines whether or not the contact pressure p1, p2 changing over time is within the pressure reference range p0. For example, in the first graph of FIG. 6A, since the contact pressure p1 at the first time t1 exceeds the pressure reference range p0, the determination control part 202 determines that the contact pressure as a whole is outside the pressure reference range.

In addition, a speed reference range is a range on the basis of contact speed of the touching to feel that contacted person B is comfortable. Normally, the faster the contact speed of touching, the contacted person B does not feel comfort. The comfortable touching is necessary to consider the contact speed to promote activation of the C tactile fibers conveying comfort. In the present invention, the speed reference range is set to a range of 1 cm/sec-20 cm/sec corresponding to the contact speed at which the C tactile fibers work actively. The touching within the speed reference range becomes the comfortable contact in comparison with normal contact.

The determination control part 202 compares the speed reference range v0 with the contact speed v12 of the measured value, and determines whether or not the contact speed v12 is within the speed reference range v0. In addition, there is not the limitation in particular in order of the determination of the contact pressure and the contact speed in the determination control part 202.

When the determination control part 202 completes the determination, finally, an evaluation control part 203 of the terminal device 12 evaluates that the touching of the contacting person A is a comfortable touching when all the measured values are within corresponding reference ranges respectively, and evaluates that the touching of the contacting person A is an uncomfortable touching when one measured value is outside the corresponding reference range (FIG. 4: S103).

The evaluation method of the evaluation control part 203 is not particularly limited. For example, when the contact pressure is within the pressure reference range and the contact speed is within the speed reference range, then all the measured values are within corresponding reference ranges respectively. So, the evaluation control part 203 evaluates the touching of the contacting person A is a comfortable touching, and displays the comfortable touching on the panel. In this way, the contacting person A or the leader can confirm that the touching of the contacting person A is a comfortable touching.

In addition, the evaluation control part 203 may display the values of the contact pressure and the contact speed in addition to the display of the comfortable touching, a graph indicating a change over time of the contact pressure detected by the sensor 11, a pressure reference range, and graphically displays the contact pressure and the contact speed with illustrations, animations, etc. In this way, contacting person A or the leader can recognize the touching of the contacting person A with the values objectively.

The comfortable touching requires that all the measured values of the contact pressure and the contact speed meet their respective reference ranges. If even one of them does not meet the reference range, the touching is not a comfortable touching and becomes an uncomfortable touching.

For example, when the contact pressure is outside the pressure reference range and the contact speed is within the speed reference range, one measured value of the contact pressure is outside the corresponding pressure reference range. So, the evaluation control part 203 evaluates the touching of the contacting person A is an uncomfortable touching, and displays the uncomfortable touching on the panel. In this way, the contacting person A or the leader can confirm that the touching of the contacting person A is an uncomfortable touching.

For example, in the contact pressure, because the contact pressure p1 of the first time t1 is outside the pressure reference range p0 in the first graph of FIG. 6A, it is possible to evaluate the touching of the contacting person A is an uncomfortable touching at that time. In the next graph of FIG. 6A, because the contact pressure p2 of the second time t2 is outside the pressure reference range p0, the touching by the contacting person A at this time is an uncomfortable touching. In the last graph of FIG. 6A, when the contact pressures p1 and p2 at the first time t1 and the second time t2 are both outside the pressure reference range p0, the touching of the contacting person A at all times is an uncomfortable touching. In these cases, even if the contact speed is within the speed reference range, the touching by the contacting person A is evaluated as uncomfortable touching as a whole. After confirming these evaluation results and graphs, the contacting person A can reduce the contact pressure or slow down the contact speed at which timing when touching next time, it is possible to be closer the touching to the comfortable touching.

When completing the evaluation, the evaluation control part 203 stops starting of two sensors 11, and completes the evaluation of the touching.

For example, when the contacting person A inputs the evaluation key into the terminal device 12 again, and touches to the touching base material 10 by hand while adjusting the touching after referring to the evaluation results, the measurement control part 201 measures contact pressures and contact speed of the hand based on the signals from the two sensors 11 (FIG. 4: S101). Here, the two contact pressures p1 and p2 and the one contact speed v12 are measured by the hand of the contacting person A sequentially contacting the two sensors 11.

Next, as shown in FIG. 6B, the determination control part 202 displays a graph which assumed the contact pressure as a vertical axis, and the graph assumed the time as a cross axle, and determines whether or not the contact pressure p1, p2 changing over time is within the pressure reference range p0. Here, since the contact pressures p1 and p2 at all times t1 and t2 are within the pressure reference range p0 respectively, the determination control part 202 determines that the contact pressures are within the pressure reference range respectively.

In addition, the determination control part 202 determines whether or not the contact speed v12 is within the speed reference range v0. Here, the contact speed v12 is within the speed reference range v0, so the determination control part 202 determines the contact speed is within the speed reference range.

In this case because the contact pressures are within the pressure reference range respectively and the contact speed is within the speed reference range, all the measured values are within corresponding reference ranges respectively. So, the evaluation control region 203 evaluates the touching of the contacting person A with a comfortable touching and displays the comfortable touching on the panel. In this way, it is possible to be closer the touching to the comfortable touching by the contacting person A repeating the evaluation of the touching.

Thus, because the contact pressures and the contact speed of the hand of the contacting person A are within the reference ranges respectively, it is possible to determine that the touching of the contacting person A is believed to make contacted person B feel comfortable in a short time and surely. And, it is possible to evaluate a touching skill level of the contacting person A for each measured value objectively, and to confirm the reproducibility of the touching of the contacting person A. By digitizing the contact pressures and the contact speed of the touching, it is possible to manage an accuracy of the touching of the contacting person A.

The evaluation of such a touching is applicable to a service that a person touches a person such as caring, baby touching, baby massage, cultivation of aesthetic sensitivity of child, beauty, or the like, as well as nursing widely. In addition, it is possible to efficiently learn comfortable touching (touch care) of the contacting person A. The contacting person A is not limited to human, for example, a development of the human robot touching with human can be applied.

By the way, when the touching base material 10 and sensors 11 are touch panel P of touch panel type terminal device 12, the contact speed is measured as follows. As shown in FIG. 7A, when the hand of the contacting person A touches to the touch panel P, the measurement control part 201 detects a touching of the hand of the contacting person A at the first contact position 11, and measures a contact pressure p1 (kgf/cm2) and a contact position x1 (cm), y1 (cm) of the hand of the contacting person A at the first contact time t1 (sec) based on the signal from the contact position 11. The method of determining the contact position x1 (cm), y1 (cm) is not particularly limited. For example, a method of determining the position from a preset reference point on the surface of the touch panel P to the contact position can be used.

Next, when the hand of the contacting person A continues to touch to the touch panel P, the measurement control part 201 detects a touching of the hand of the contacting person A at the next contact position 11, and measures a contact pressure p2 (kgf/cm2) and a contact position x2 (cm), y2 (cm) of the hand of the contacting person A at the second contact time t2 (sec) based on the signal from the contact position 11. Here, a contact speed of the hand of the contacting person A can be measured by measuring the two contact positions 11 at each contact time. For example, the measurement control part 201 calculates a time interval Δt12 (sec) between the first contact time t1 and the second contact time t2, and calculates a position interval d12 (cm) between the first contact position 11 and the second contact position 11. The position interval d12 (cm) between the first contact position 11 and the second contact position 11 can be calculated by the following formula (1).

$$d12=\sqrt{\{(x2-x1)2+(y2-y1)2\}} \quad (1)$$

And the measurement control part 201 can calculate the contact speed v12 (cm/sec) of the hand of the contacting person A passed two contact position 11 by dividing the position interval d12 (cm) by the time interval Δt12 (sec).

In addition, when the plural contact positions detected on touch panel P cannot be detected linearly due to specifications of the touch panel P, the plural contact positions detected non-linearly may be linearly corrected, and the corrected contact positions may be used.

In addition, the case where there are two contact positions has been described in the above, in the case where two or more sensors 11 are arranged or in the case of the touch panel P, it is as follows. As shown in FIG. 7B, for example, when six sensors 11 are installed linearly or nearly linearly at a predetermined interval on the touching base material 10, when the hand of the contacting person A touches from the first sensor 11 to the sixth sensor 11 sequentially, the measurement control part 201 detects the maximum value of the contact pressure at each time t1 to t6 among the mountain-shaped contact pressure based on the signals from the respective sensors 11. Next, the measurement control part 201 calculates a time interval Δt12 at the start time when leadings of the contact pressure detected by the first sensor 11 and second sensor 11 are started, divides a position interval d12 (cm) between the first sensor 11 and the second sensor 11 by the time interval Δt12 (sec), and calculates a first contact speed v12 (cm/sec). Similarly, the measurement control part 201 calculates a contact speed v (cm/sec) of the hand of the contacting person A passed through these two sensors 11 based on a time interval at the start time when leadings of the contact pressure detected by the two adjacent sensors 11 are started, and a position interval between the two adjacent sensors 11. In this way, when those are six sensors 11, it is possible to measure five contact speeds to change over time. By increasing the number of sensors 11, it is possible to confirm change over time of the contact speed of touching in more detail. In addition, in the case of touch panel P, it is similar. And if all five contact speeds are within the speed reference range v0 respectively, the determination control part 202 determines that the contact speeds are within the speed reference range.

In the above, the element of the comfortable touching was set to the minimum necessary contact pressures and contact speed. By further increasing this element, it is possible to evaluate the comfortable touching with high accuracy.

For example, for other element of the comfortable touching, it is possible to add a contact attachment indicating a contact area of the hand of the contacting person A. In this case, the measurement control part 201 measures a contact attachment of the hand of the contacting person A as a measured value based on sensor 11 more. For example, when two or more sensors 11 are arranged in a straight line, it is possible to measure a multiplied value obtained by multiplying an installation interval between a predetermined number of sensors 11 that have transmitted signals by a width of the hand of the contacting person A as the contact attachment (contact area) of the contacting person A when the hand of the contacting person touches to the predetermined number of sensors 11. Further, when the touch panel P functions as the sensor 11, it is possible to measure an area indicated by a plurality of contact positions where the hand of the contacting person A touches and the touch panel P transmits signals as the contact attachment. The determination control part 202 determines whether or not the measured value is within a contact attachment reference range using the contact attachment reference range corresponding to the attachment.

Here, for the touching of the whole body except the face, the contact attachment reference range is a range of 24 cm2-400 cm2. For the touching of the face, the contact attachment reference range is a range of 1 cm2-100 cm2. When the contact attachment is about 1 cm2, the touching with finger pad is assumed. When the contact attachment is about 24 cm2, the touching with a palm of a small contacting person A is assumed. When the contact attachment is about 400 cm2, the touching with a palm and five fingers of a large contacting person A is assumed.

As shown in FIG. 8A, when a plurality of sensors 11 are provided with a predetermined interval d at positions on a specific line having a predetermined width along dermatome or muscle run of the forearm of the human phantom 10, when the hand of the contacting person A touches to the predetermined number of sensors 11, the measurement control part 201 measures the contact pressures and the contact speed based on the signals from the sensors 11, and measures a multiplied value obtained by multiplying the installation interval d of the sensors 11 that transmitted the signals by the size of the hand width w of the contacting person A as the contact attachment (contact area) of the contacting person A.

Because a contact surface A1 of the palm of contacting person A touches to the human phantom 10 in a state straddling two sensors 11, for example, as the minimum of the contact attachment, by multiplying the installation interval d between the two sensors 11 by the width w of the palm of the contacting person A, assuming that the palm is a rectangle, it is possible to measure the contact attachment A (d×w) of the contacting person A.

As shown in FIG. 8B, when a sheet-shaped composite sensor 11 capable of measuring pressure, position, and attachment is provided on an outer peripheral surface of the forearm of the human phantom 10 like the touch panel P, when the palm of the contacting person A touches to the sheet-shaped composite sensor 11, the measurement control part 201 measures the contact pressures and the contact speed based on the signals from the sensor 11, and measures the contact attachment of the contacting person A by calculating an area indicated by the sheet-shaped signal generation positions of the sensor 11. In the above description, the spot-shaped or sheet-shaped sensor 11 was explained as an example. the method for measuring the attachment of the contacting person A may be appropriately set according to the type and shape of the sensor 11.

Here, a contact attachment reference range is a range on the basis of contact attachment of the touching to feel that contacted B is comfortable. The contact attachment of the touching means that the contact surface A1 of the palm of the contacting person A is in close contact with the skin B1 of the contacted person B. If the contact attachment of the touching is too low, the contacted B feels unsatisfactory or tickled. The contacting person A can increase the contact attachment by contacting with the contact surface A1 of the palm sufficiently. When a contact temperature is within the temperature reference range, the warmth of the contact surface A1 of the palm of the contacting person A is transmitted to the contacted person B, and the touching becomes a comfortable touching. As a device to increase the contact attachment it is good that the contacting person A relaxes and contacts to the contact surface A1 of the palm into close contact with the skin B1 of the contacted person B sufficiently.

In this invention, when the contacting person A is Japanese, the contact attachment reference range is a range of 24 cm2-200 cm2, for example. As an example of how to obtain the attachment, when the contacting person A touches only with the palm, the hand width of the small contacting person A (for example, a 4-year-old child) is about 4 cm, the third finger of the palm from the wrist to the base of the third finger is about 6 cm, so a palm area of the small contacting person A is 4 cm×6 cm=24 cm2. When the large contacting person A touches only with the palm, the hand width of the large contacting person A (for example, an adult male) is about 10 cm, the third finger of the palm is about 10 cm, so a palm area of the large contacting person A is 10 cm×10 cm=100 cm2. If the touching is performed with the palm and five fingers, the touching is extremely wide contact compared to normal contact. The area of the hand varies depending on race, for example, the attachment reference range is set to a range of 24 cm 2 to 400 cm 2 according to race.

Thus, when the contact pressures, the contact speed, and the contact attachment of the measured values are measured, the determination control part 202 determines whether or not the measured value is within the reference range for each of measured values. For example, the determination control part 202 displays a touching mode of the body and a touching mode of the face selectably, and determines the contact attachment using the contact attachment reference range of the mode selected by contacting person A. When all the measured values are within corresponding reference ranges respectively, the evaluation control part 203 evaluates that the touching of the contacting person A is a comfortable touching.

As above, when one measured value of all the measured values is outside the corresponding reference range, the evaluation control part 203 evaluates that the touching of the contacting person A is an uncomfortable touching, and displays the uncomfortable touching on the panel. In this way, by increasing the types of measured values, it is possible to evaluate comfortable touching with high accuracy.

Here, for other element of the comfortable touching, it is possible to add a contact temperature of the hand of the contacting person A. In this case, the measurement control part 201 measures a contact temperature of the hand of the contacting person A as a measured value based on a temperature sensor 11 more. The determination control part 202 determines whether or not the measured value is within a contact temperature reference range using the contact temperature reference range corresponding to the contact temperature. The contact temperature reference range is a range of 25 degrees-45 degrees.

When the measurement control part 201 measures the contact temperature, the sensor 11 may be provided with a temperature sensor separately in addition to the pressure sensor and the position sensor, or a composite sensor 11 that combines a pressure sensor, a position sensor and a temperature sensor may be used. When the sensor is the elastic composite sensor 11, the contact temperature of the hand may be measured from a recessed part of the composite sensor 11 caused by the touching of the contacting person A.

Here, the temperature reference range is a range on the basis of contact temperature of the touching to feel that contacted B is comfortable. When contact temperature of the touching is too high, a heat pain receptor of the skin begins to work activity, and the touching becomes hot uncomfortable touching. When the contact temperature of the touch is too low, a cold receptor of the skin begins to work activity, and the touching becomes cold uncomfortable touching.

For the comfortable touching, it is necessary to consider C tactile fibers and warm receptor to introduce comfort not the activity of the heat pain receptor and the cold receptor. In the present invention, the temperature reference range is set to the range of 25 degrees to 45 degrees, corresponding to the contact temperature at which the C tactile fibers and warm receptor are active. The touching within this temperature reference range results in a warm comfortable touching compared to normal touching.

When the contact pressures, the contact speed, and the contact temperature of the measured values are measured, the determination control part 202 determines whether or not the measured value is within the reference range for each of measured values. When all the measured values are within corresponding reference ranges respectively, the evaluation control part 203 evaluates that the touching of the contacting person A is a comfortable touching.

For example, when the contact pressure is outside the pressure reference range, the contact speed is within the speed reference range and the contact temperature is within the temperature reference range, one measured value of all the measured values is outside the corresponding reference range. Thus, the evaluation control part 203 evaluates that the touching of the contacting person A is an uncomfortable touching, and displays the uncomfortable touching on the panel. In this way, by increasing the types of measured values, it is possible to evaluate the comfortable touching with high accuracy.

In addition, for other element of the comfortable touching, it is possible to add a contact path (contact route) of a running of the hand of the contacting person A on a skin of the contacted person B.

For example, when the touching base material 10 is the human phantom 10, it is easy to measure the contact route. As shown in FIG. 9, when two or more sensors 11 are provided with a predetermined interval d at positions on a specific line having a predetermined width along the running of dermatome or muscle run of the forearm of human phantom 10, when the contact surface A1 of the hand of the contacting person A touches to a predetermined number of sensors 11, the measurement control part 201 can measure a contact route based on signal positions and a switching time interval of the signals of the predetermined number of sensors 11 using the signals from the sensors 11.

In FIG. 9, the contact surface A1 of the hand of the contacting person A first touches to the human phantom 10 in a state straddling two sensors 11, and gradually touches to the sensors 11 from the base to the tip of the human phantom 10. In this case, the measurement control part 201 can measure a multiplied value obtained by dividing a installation interval d (cm) by a time interval t (sec) as the contact speed (cm/sec) based on the time interval t (sec) for switching from the signal of the first sensor 11 toward the tip of the human phantom 10 to the signal of the next sensor 11, and the installation distance d (cm) between the first sensor 11 and the next sensor 11.

As shown in FIG. 9, when a plurality of sensors 11 are sequentially provided at positions on the specific line having the predetermined width along dermatome or muscle run in the human phantom 10, when the contact surface A1 of the hand of the contacting person A touches to the plurality of sensors 11, the measurement control part 201 can measure the contact route of the contact surface A1 of the hand of the contacting person A based on the positions and the order of the sensors 11 emitting signals.

When signals of the sensors 11 provided on the specific line are sequentially received in the forward or reverse direction of the specific line from the base to the tip of the human phantom 10, the contact route of the contact surface A1 of the hand of the contacting person A runs along the specific line, and it is possible to measure that the contact route is on the line. Otherwise, when signals of the sensors 11 provided on the specific line are not sequentially received in the forward or reverse direction of the specific line from the base to the tip of the human phantom 10, for example, when the signal from the sensor 11 is partially missing and the signals received intermittently, the contact route of the contact surface A1 of the hand of the contacting person A does not run on the specific line, and it is possible to measure that the contact route is off-line (out of the line).

Here, when the contact pressures, the contact speed, the and contact route of the measured values are measured, the determination control part 202 determines whether or not the measured value is within the reference range for each of measured values. When all the measured values are within corresponding reference ranges respectively, the evaluation control part 203 evaluates that the touching of the contacting person A is a comfortable touching. As above, when one measured value of all the measured values is outside the corresponding reference range, the evaluation control part 203 evaluates that the touching of the contacting person A is an uncomfortable touching. For example, the contact route reference range corresponding to the contact route is on the line. In this way, by increasing the types of measured values, it is possible to evaluate comfortable touching with high accuracy.

The elements of the comfortable touching can adopt one or combination on the contact attachment, the contact temperature, or the contact route in addition to the contact pressure and the contact speed. The elements of the comfortable touching may be called PARTS by taking the initials of Pressure, Attachment, Route, Temperature and Speed.

In the present invention, the terminal device 12 is configured to have each control part, a storage medium may store a program for realizing each of the control parts, and the storage medium may be provided. In this configuration, the program is read by a predetermined terminal device, and the terminal device realizes each control part. In that case, the program itself read from the recording medium exhibits the effects of the present invention. The program is the same whether it is an application downloadable from a network or cloud computing.

It is also possible to provide the steps executed by each control part as a touching evaluation method according to the present invention. For example, a leader uses a human phantom 10 with a built-in sensor 11 to perform touching to the contacting person A, and makes the contacting person A perform touching. The method may measure the contact pressure and the contact speed by the sensor 11, determine whether or not the measured values are within the reference range, and evaluate whether the touch is comfortable or uncomfortable.

EXAMPLE

The present invention will be specifically described below by way of Examples and Comparative examples, and the present invention is not limited thereby.

<Method of the Touching>

About touching, based on the contact pressure and the contact speed, the contacting person touched to the contacted person, and evaluated the touching by confirming the comfort of the contacted person. First, the contacting person touched to a forearm of the contacted person (corresponding to the whole body) with a hand. The contacted person was a woman in her 50s. Examples and Comparative examples were carried out using the contact pressure and the contact speed as indicators.

Before and after touching, VAS (Visual Analog Scale) is performed on the contacting person, and it is calculated the difference by subtracting the before performance by the after performance. When the difference was a positive value, the touching was evaluated as a comfortable touching, and when the difference was a negative value, the touching was evaluated as an uncomfortable touching.

<Evaluation Result of the Touching>

FIG. 10 shows an evaluation condition and an evaluation result of touching of Example 1-4 and Comparison example 1-5. When the difference was 10 or more, it was evaluated as "0" of a comfortable evaluation, and when the difference was less than 10, it was evaluated as "X" of an uncomfortable evaluation. As shown in FIG. 10, when the contact pressure is within the range of 0.001 kg/cm2-2.000 kg/cm2 and the contact speed is within the range of 1 cm/sec-20 cm/sec, it turned out that the touching becomes comfortable. Otherwise, it turned out that the touching becomes uncomfortable. Therefore, it was found that the contact pressure and the contact speed are important in the touching.

Next, using the contact pressure, the contact speed, the contact temperature, the contact attachment, and the contact route as indicators, the contacting person touched to the contacted person, confirmed the comfort of the contacted person, and performed VAS in the same manner as described above to evaluate the touching. The contact temperature was varied by heating the hand of the contacting person with a heating means or by cooling it with a cooling means. In touching of the palm of the contacting person, the hand width of the contacting person is about 7.0 cm, and the length of the third finger of the palm is about 7.5 cm, and the contact attachment of the palm of the contacting person is set to 52.5 cm2. In the touching of three fingers of the hand of the contacting person, the length of the three fingers of the contacting person is about 2.0 cm, and the width of the three fingers is about 4.0 cm, and the contact attachment of the contact part of the contacting person is 8.0 cm2. In the touching of one finger of the hand of the contacting person, the length of one finger of the contacting person is about 2.0 cm and the width of one finger is about 1.2 cm, and the contact attachment of the contact part of the contacting person is 2.4 cm2. In the touching of the palm and five fingers of the contacting person, the length of the palm and middle finger of the contacting person is about 17.0 cm, the width of the hand is about 7 cm, and the contact attachment of the palm and five fingers of the contacting person is 119.0 cm2. As shown in FIG. 9, the contact route was on a specific line of a predetermined width along dermatome or muscle run, or others. For example, out-of-lines of others were on dermatome borders, on muscle borders, or in a meandering curve.

<Evaluation Result of the Touching>

FIG. 11 shows an evaluation condition and an evaluation result of touching of Example 5-11. When the difference was 10 or more and 20 or less, it was evaluated as "0" of the comfortable evaluation. When the difference exceeded 20, it was evaluated as "A" of the most comfortable evaluation. As shown in FIG. 11, in addition to the contact pressure and the contact speed, the contact attachment is within the range of 24 cm2-400 cm2, the contact temperature is within the range of 25 degrees-45 degrees, and the contact route is on the specific line of predetermined width along dermatome or muscle run, it turned out that the touching becomes comfortable. Otherwise, it turned out that the touching becomes a slightly uncomfortable. Therefore, it was found that it is important to add the contact attachment, the contact temperature and the contact route to the contact pressure and the contact speed in order to improve the quality of comfortable touching.

Next, changing the contact target of the contacted person from the forearm to the face, using the contact pressure and the contact speed, the contacting person touched to the contacted person, confirmed the comfort of the contacted person, and performed VAS in the same manner as described above to evaluate the touching.

<Evaluation Result of the Touching>

FIG. 12 shows an evaluation condition and an evaluation result of touching of Example 12-15 and Comparison example 7-9. When the difference was 10 or more, it was evaluated as "0" of a comfort evaluation, and when the difference was less than 10, it was evaluated as "X" of an uncomfortable evaluation. As shown in FIG. 12, when the contact target is the face, and when the contact pressure is within the range of 0.001 kg/cm2-1.000 kg/cm2 and the contact speed is within the range of 1 cm/sec-20 cm/sec, it turned out that the touching becomes comfortable. Otherwise, it turned out that the touching becomes uncomfortable.

Next, using the contact pressure, the contact speed, the contact temperature, and the contact attachment as indicators, the contacting person touched to the contacted person, confirmed the comfort of the contacted person, and performed VAS in the same manner as described above to evaluate the touching.

<Evaluation Result of the Touching>

FIG. 13 shows an evaluation condition and an evaluation result of touching of Example 16-19 and Comparison example 10-12. When the difference was 10 or more and 20 or less, it was evaluated as "0" of the comfortable evaluation. When the difference exceeded 20, it was evaluated as "A" of the most comfortable evaluation. As shown in FIG. 13, when the contact target is the face, in addition to the contact pressure and the contact speed, the contact attachment is within the range of 1 cm2-100 cm2, and the contact temperature is within the range of 25 degrees-45 degrees, it turned out that the touching becomes comfortable. Otherwise, it turned out that the touching becomes a slightly uncomfortable. Therefore, it was found that it is important to add the contact attachment and the contact temperature to the contact pressure and the contact speed in order to improve the quality of comfortable touching.

INDUSTRIAL APPLICABILITY

As described above, the touching evaluation device and the touching evaluation method are useful to evaluate comfortable touching objectively. It is effective as the touching evaluation device and the touching evaluation method that can evaluate a touching with high accuracy based on a reference of the touching to cause comfort. It is possible to record and utilize a comfortable touching.

REFERENCE SIGNS LIST

1 TOUCHING EVALUATION DEVICE
10 HUMAN PHANTOM
11 SENSORS
12 TERMINAL DEVICE
201 MEASUREMENT CONTROL PART
202 DETERMINATION CONTROL PART
203 EVALUATION CONTROL PART

The invention claimed is:

1. A touching evaluation device comprising:

a touching base material having a semi-cylindrical shape, a half-polygonal shape, a semi-elliptical prism shape, or a human phantom representing a right forearm, a left forearm, a back of a right hand, a back of a left hand, a right palm, a left palm, a face, or a whole body;

at least two sensors installed at a predetermined interval on an outer peripheral surface of the touching base material;

a terminal device having a CPU and a ROM;

a measurement control part executed by the CPU and configured to measure contact pressures and a contact speed of a hand of a contacting person, the contact pressures changing over time at respective positions, as measured values respectively based on the two sensors when the hand of the contacting person touches the two sensors sequentially, the two sensors being capable of detecting a contact pressure in at least two different positions;

a determination control part executed by the CPU and configured to compare the measured values with reference ranges respectively, the reference ranges predetermined for a contacted person feeling comfortable when touched by the contacting person, and determining whether or not the measured value is within the reference range for each of the measured values; and an evaluation control part executed by the CPU and configured to evaluate that the touching of the contacting person is a comfortable touching when all the measured values are within corresponding reference ranges respectively, and evaluating that the touching of the contacting person is an uncomfortable touching when one measured value is outside the corresponding reference range;

wherein:

a pressure reference range corresponding to the contact pressure for the touching of a whole body except a face of the contacting person is a range of 0.001 kgf/cm^2-2.000 kgf/cm^2, and the pressure reference range for the touching of the face is a range of 0.001 kgf/cm^2-1.000 kgf/cm^2, a contact reference speed corresponding to the contact speed is a range of 1 cm/sec-20 cm/sec and the pressure reference range and the contact reference speed are stored in the ROM.

2. The touching evaluation device according to claim 1, wherein:

the measurement control part measures a maximum pressure value from a temporal change in the contact pressure detected by the sensor as the contact pressure of the hand of the contacting person.

3. The touching evaluation device according to claim 1, wherein:

the measurement control part calculates the contact speed of the hand of the contacting person by dividing a distance between the two sensors by a time interval between start times of detection of contact pressure by the two sensors.

4. The touching evaluation device according to claim 1, wherein:

the measurement control part measures a maximum pressure value from a temporal change in the contact pressure detected by the sensor as the contact pressure of the hand of the contacting person, and calculates the contact speed of the hand of the contacting person by dividing a distance between the two sensors by a time interval between start times of detection of contact pressure by the two sensors.

5. The touching evaluation device according to claim 1, wherein:

the touching base material is made of a flexible material including synthetic resin or an elastic material including sponge or rubber.

6. The touching evaluation device according to claim 1, wherein:

a pressure reference range for a touching mode of a body is a range of 0.001 kgf/cm^2-2.000 kgf/cm^2, and the pressure reference range for a touching mode of a face is a range of 0.001 kgf/cm^2-1.000 kgf/cm^2, and the determination control part displays the touching mode of the body and the touching mode of the face for selection, and determines whether or not the contact pressure is within the reference range corresponding to the touching mode selected by the contacting person.

7. The touching evaluation device according to claim 1, wherein:

the touching base material is made of a flexible material including synthetic resin or an elastic material including sponge or rubber, a pressure reference range for a touching mode of a body is a range of 0.001 kgf/cm^2-2.000 kgf/cm^2, and the pressure reference range for a touching mode of a face is a range of 0.001 kgf/cm^2-1.000 kgf/cm^2, and the determination control part displays the touching mode of the body and the touching mode of the face for selection, and determines whether or not the contact pressure is within the reference range corresponding to the touching mode selected by the contacting person.

8. The touching evaluation device according to claim 1, wherein:

the determination control part displays a graph having contact pressure detected by the two sensors on a vertical axis and time on a horizontal axis, sets the pressure reference range to the graph, and determines whether or not the contact pressure changing over time is within the reference range.

9. The touching evaluation device according to claim 1, wherein:

a pressure reference range for a touching mode of a body is a range of 0.001 kgf/cm^2-2.000 kgf/cm^2, and the pressure reference range for a touching mode of a face is a range of 0.001 kgf/cm^2-1.000 kgf/cm^2, the determination control part displays the touching mode of the body and the touching mode of the face for selection, displays a graph having contact pressure detected by the two sensors on a vertical axis and time on a horizontal axis, sets the pressure reference range to the graph, and determines whether or not the contact pressure changing over time is within the reference range.

10. The touching evaluation device according to claim 1, wherein:

the determination control part displays a graph having contact pressure detected by the two sensors on a vertical axis and time on a horizontal axis, sets the pressure reference range to the graph, and determines whether or not the contact pressure changing over time is within the reference range, and the evaluation control part displays at least one of a value of the contact pressure, a value of the contact speed, a graph indicating a change over time of the contact pressure detected by the sensor, or the pressure reference range, and graphically displays the contact pressure or the contact speed.

11. The touching evaluation device according to claim 1, wherein:

a pressure reference range for a touching mode of a body is a range of 0.001 kgf/cm^2-2.000 kgf/cm^2, and the pressure reference range for a touching mode of a face is a range of 0.001 kgf/cm^2-1.000 kgf/cm^2, the determination control part displays the touching mode of the body and the touching mode of the face for selection, and determines whether or not the contact pressure is within the reference range corresponding to the touching mode selected by the contacting person, and the evaluation control part displays at least one of a value of the contact pressure, a value of the contact speed, a graph indicating a change over time of the contact pressure detected by the sensor, or the pressure reference range, and graphically displays the contact pressure or the contact speed.

12. The touching evaluation device according to claim 1, wherein:

the touching base material is made of a flexible material including synthetic resin or an elastic material including sponge or rubber, a pressure reference range for a touching mode of a body is a range of 0.001 kgf/cm^2-2.000 kgf/cm^2, and the pressure reference range for a touching mode of a face is a range of 0.001 kgf/cm^2-1.000 kgf/cm^2, the determination control part displays the touching mode of the body and the touching mode of the face for selection, and determines whether or not the contact pressure is within the reference range corresponding to the touching mode selected by the contacting person, and the evaluation control part displays at least one of a value of the contact pressure, a value of the contact speed, a graph indicating a change over time of the contact pressure detected by the sensor, or the pressure reference range, and graphically displays the contact pressure or the contact speed.

13. The touching evaluation device according to claim 1, wherein:

the touching evaluation device is used for one of nursing, caring, baby touching, baby massage, cultivation of aesthetic sensitivity of child, beauty, or development of touching between a human and a robot.

14. The touching evaluation device according to claim 1, wherein:

when the sensor includes a temperature sensor, the measurement control part measures a contact temperature of the hand of the contacting person based on the temperature sensor, and a temperature reference range corresponding to the contact temperature is a range of 25 degrees-45 degrees.

15. A touching evaluation method of a touching evaluation device, the touching evaluation device comprising:

a touching base material having a semi-cylindrical shape, a half-polygonal shape, a semi-elliptical prism shape, or a human phantom representing a right forearm, a left forearm, a back of a right hand, a back of a left hand, a right palm, a left palm, a face, or a whole body;

at least two sensors installed at a predetermined interval on an outer peripheral surface of the touching base material; and a terminal device having a CPU and a ROM;

the touching evaluation method comprising:

a measurement control step performed by a CPU for measuring contact pressures and a contact speed of a hand of a contacting person, the contact pressures changing over time at respective positions, as measured values respectively based on the two sensors when the hand of the contacting person touches the two sensors sequentially, the two sensors being capable of detecting a contact pressure in at least two different positions;

a determination control step performed by a CPU for comparing the measured values with reference ranges respectively, the reference ranges predetermined for a contacted person feeling comfortable when touched by the contacting person, and determining whether or not the measured value is within the reference range for each of the measured values; and an evaluation control step performed by a CPU for evaluating that the touching of the contacting person is a comfortable touching when all the measured values are within corresponding reference ranges respectively, and evaluating that the touching of the contacting person is an uncomfortable touching when one measured value is outside the corresponding reference range;

wherein:

a pressure reference range corresponding to the contact pressure for the touching of a whole body except a face of the contacting person is a range of 0.001 kgf/cm^2-2.000 kgf/cm^2, and the pressure reference range for the touching of the face is a range of 0.001 kgf/cm^2-1.000 kgf/cm^2, a contact reference speed corresponding to the contact speed is a range of 1 cm/sec-20 cm/sec and the pressure reference range and the contact reference speed are stored in the ROM.

16. The touching evaluation method according to claim 15, wherein:

when the sensor includes a temperature sensor, the measurement control step measures a contact temperature of the hand of the contacting person based on the temperature sensor, and a temperature reference range corresponding to the contact temperature is a range of 25 degrees-45 degrees.

17. The touching evaluation method according to claim 15, wherein:

the touching evaluation method is used for one of nursing, caring, baby touching, baby massage, cultivation of aesthetic sensitivity of child, beauty, or development of touching between a human and a robot.

18. A non-transitory computer-readable medium storing a program for causing a computer to execute a touching evaluation method of a touching evaluation device, the touching evaluation device comprising:

a touching base material having a semi-cylindrical shape, a half-polygonal shape, a semi-elliptical prism shape, or a human phantom representing a right forearm, a left forearm, a back of a right hand, a back of a left hand, a right palm, a left palm, a face, or a whole body;

at least two sensors installed at a predetermined interval on an outer peripheral surface of the touching base material; and a terminal device having a CPU and a ROM;

the method comprising:

a measurement control step performed by a CPU for measuring contact pressures and a contact speed of a hand of a contacting person, the contact pressures changing over time at respective positions, as measured values respectively based on the two sensors when the hand of the contacting person touches the two sensors sequentially, the two sensors being capable of detecting a contact pressure in at least two different positions;

a determination control step performed by a CPU for comparing the measured values with reference ranges respectively, the reference ranges predetermined for a contacted person feeling comfortable when touched by the contacting person, and determining whether or not the measured value is within the reference range for each of the measured values; and an evaluation control step performed by a CPU for evaluating that the touching of the contacting person is a comfortable touching when all the measured values are within corresponding reference ranges respectively, and evaluating that the touching of the contacting person is an uncomfortable touching when one measured value is outside the corresponding reference range;

wherein:

a pressure reference range corresponding to the contact pressure for the touching of a whole body except a face of the contacting person is a range of 0.001 kgf/cm^2-2.000 kgf/cm^2, and the pressure reference range for the touching of the face is a range of 0.001 kgf/cm^2-1.000 kgf/cm^2, a contact reference speed corresponding to the contact speed is a range of 1 cm/sec-20 cm/sec and the pressure reference range and the contact reference speed are stored in the ROM.

19. The program according to claim 18, wherein:

when the sensor includes a temperature sensor, the measurement control step measures a contact temperature of the hand of the contacting person based on the temperature sensor, and a temperature reference range corresponding to the contact temperature is a range of 25 degrees-45 degrees.

20. The program according to claim 18, wherein:

the touching evaluation method is used for one of nursing, caring, baby touching, baby massage, cultivation of aesthetic sensitivity of child, beauty, or development of touching between a human and a robot.

* * * * *